United States Patent [19]

Hollister

[11] Patent Number: 5,232,455
[45] Date of Patent: Aug. 3, 1993

[54] SYRINGE WITH PROTECTIVE HOUSING

[75] Inventor: William H. Hollister, Nelson, N.H.

[73] Assignee: Smiths Industries Medical Systems, Inc., Keene, N.H.

[21] Appl. No.: 637,880

[22] Filed: Jan. 7, 1991

[51] Int. Cl.5 .............................................. A61M 5/32
[52] U.S. Cl. ................................... 604/192; 604/263; 604/110
[58] Field of Search .............. 604/110, 162, 167, 192, 604/197, 198, 263

[56] References Cited

U.S. PATENT DOCUMENTS

| | | |
|---|---|---|
| 1,779,451 | 10/1930 | Sponsel . |
| 2,700,385 | 1/1955 | Ortiz . |
| 2,836,942 | 6/1958 | Miskel . |
| 2,854,976 | 10/1958 | Heydrich . |
| 2,953,243 | 9/1960 | Roehr . |
| 3,021,942 | 2/1962 | Hamilton . |
| 3,073,307 | 1/1963 | Stevens . |
| 3,074,542 | 1/1963 | Myerson et al. . |
| 3,255,873 | 6/1966 | Speelman . |
| 3,294,231 | 12/1966 | Vanderbeck . |
| 3,323,523 | 6/1967 | Scislowicz et al. . |
| 3,324,853 | 6/1967 | Czorny et al. ........................ 604/162 |
| 3,329,146 | 7/1967 | Waldman, Jr. . |
| 3,333,682 | 8/1967 | Burke . |
| 3,367,488 | 2/1968 | Hamilton . |
| 3,485,239 | 12/1969 | Vanderbeck . |
| 3,537,452 | 11/1970 | Wilks . |
| 3,610,240 | 10/1971 | Harautuneian . |
| 3,658,061 | 4/1972 | Hall . |
| 3,828,775 | 8/1974 | Armel . |
| 3,890,971 | 6/1975 | Leeson et al. . |
| 3,904,033 | 9/1975 | Haerr . |
| 3,934,722 | 1/1976 | Goldberg .............................. 206/365 |
| 3,968,876 | 7/1976 | Brookfield . |
| 4,113,090 | 9/1978 | Carstens .............................. 206/365 |
| 4,139,009 | 2/1979 | Alvarez . |
| 4,175,008 | 11/1979 | White . |
| 4,300,678 | 11/1981 | Gyure et al. ......................... 206/364 |
| 4,375,849 | 3/1983 | Hanifl .................................. 206/366 |
| 4,430,082 | 2/1984 | Schwabacher ....................... 604/263 |
| 4,592,744 | 6/1986 | Jagger et al. ......................... 604/192 |
| 4,634,428 | 1/1987 | Cuu ..................................... 604/110 |
| 4,643,722 | 2/1987 | Smith, Jr. ............................. 604/192 |
| 4,659,330 | 4/1987 | Nelson et al. ........................ 604/192 |
| 4,664,259 | 5/1987 | Landis ................................. 604/192 |
| 4,664,654 | 5/1987 | Strauss ................................ 604/198 |
| 4,681,567 | 7/1987 | Masters et al. ....................... 604/198 |
| 4,695,274 | 9/1987 | Fox ...................................... 604/198 |
| 4,702,738 | 10/1987 | Spencer ............................... 604/198 |

(List continued on next page.)

FOREIGN PATENT DOCUMENTS 1233302 5/1971 United Kingdom .
87/07162 12/1987 World Int. Prop. O. .

Primary Examiner—C. Fred Rosenbaum
Assistant Examiner—Ronald Stright, Jr.
Attorney, Agent, or Firm—Pollock, Vande Sande & Priddy

[57] ABSTRACT

To provide a high degree of protection against the possibility of someone being accidentally punctured by a contaminated needle, the syringe of the present invention has directly connected thereto a protective housing, which can be pivoted to a position in alignment with the contaminated needle to envelop the same. As the housing is pivoted into the alignment position, locking mechanisms integral of the housing would fixedly retain the needle within the housing. The syringe of the present invention may be modified to include a housing containing an integral collapsible section and a sealer adapted to the distal portion of the housing such that, upon collapse of the collapsible section of the housing, the tip of the contaminated needle would penetrate into and be sealingly secured by the sealer. Another modification of the syringe of the present invention involves utilizing a collapsible hinge to connect the protective housing to the main body portion of the syringe. Upon collapse of the collapsible hinge, the longitudinal distance separating the housing from the main body of the syringe is reduced, thereby causing the tip of the contaminated needle to pierce and penetrate into the sealer and be sealingly retained thereby.

22 Claims, 7 Drawing Sheets

U.S. PATENT DOCUMENTS

| | | | |
|---|---|---|---|
| 4,723,943 | 2/1988 | Spencer | 604/198 |
| 4,728,320 | 3/1988 | Chen | 604/110 |
| 4,728,321 | 3/1988 | Chen | 604/110 |
| 4,731,059 | 3/1988 | Wanderer et al. | 604/192 |
| 4,735,311 | 4/1988 | Lowe et al. | 206/365 |
| 4,735,618 | 4/1988 | Hagan | 604/192 |
| 4,737,144 | 4/1988 | Choksi | 604/198 |
| 4,738,663 | 4/1988 | Bogan | 604/198 |
| 4,743,233 | 5/1988 | Schneider | 604/192 |
| 4,747,836 | 5/1988 | Luther | 604/198 |
| 4,747,837 | 5/1988 | Hauck | 604/198 |
| 4,772,272 | 9/1988 | McFarland | 604/198 |
| 4,778,453 | 10/1988 | Lopez | 604/110 |
| 4,781,697 | 11/1988 | Slaughter | 604/192 |
| 4,782,841 | 11/1988 | Lopez | 604/198 |
| 4,790,828 | 12/1988 | Dombrowsk et al. | 604/198 |
| 4,795,432 | 1/1989 | Karczmer | 604/110 |
| 4,795,443 | 1/1989 | Permenter et al. | 604/198 |
| 4,801,295 | 1/1989 | Spencer | 604/198 |
| 4,804,372 | 2/1989 | Laico et al. | 604/198 |
| 4,813,426 | 3/1989 | Haber et al. | 604/232 |
| 4,816,022 | 3/1989 | Poncy | 604/263 |
| 4,816,024 | 3/1989 | Sitar et al. | 604/192 |
| 4,819,659 | 4/1989 | Sitar | 604/198 |
| 4,820,277 | 4/1989 | Norelli | 604/192 |
| 4,826,490 | 5/1989 | Byrne et al. | 604/198 |
| 4,826,491 | 5/1989 | Schramm | 604/198 |
| 4,838,871 | 6/1989 | Luther | 604/192 |
| 4,842,587 | 6/1989 | Poncy | 604/198 |
| 4,846,796 | 7/1989 | Carrell et al. | 604/110 |
| 4,850,968 | 7/1989 | Romano | 604/110 |
| 4,850,976 | 7/1989 | Heinrich et al. | 604/192 |
| 4,850,977 | 7/1989 | Bayless | 604/198 |
| 4,850,978 | 7/1989 | Dudar et al. | 604/201 |
| 4,850,994 | 7/1989 | Zerbst et al. | 604/198 |
| 4,850,996 | 7/1989 | Cree | 604/198 |
| 4,858,607 | 8/1989 | Jordan et al. | 128/314 |
| 4,863,434 | 9/1989 | Bayless | 604/198 |
| 4,863,435 | 9/1989 | Sturman et al. | 604/198 |
| 4,863,436 | 9/1989 | Glick | 604/198 |
| 4,867,746 | 9/1989 | Dufresne | 604/192 |
| 4,872,552 | 10/1989 | Unger | 206/365 |
| 4,874,383 | 10/1989 | McNaughton | 604/263 |
| 4,874,384 | 10/1989 | Nunez | 604/198 |
| 4,883,469 | 11/1989 | Glazier | 604/192 |
| 4,886,503 | 12/1989 | Miller | 604/192 |
| 4,888,001 | 12/1989 | Schoenberg | 604/192 |
| 4,892,107 | 1/1990 | Haber | 604/198 |
| 4,892,521 | 1/1990 | Laico et al. | 604/192 |
| 4,900,309 | 2/1990 | Netherton et al. | 604/192 |
| 4,950,242 | 8/1990 | Alvarez | 604/110 |
| 4,982,842 | 1/1991 | Hollister | 604/192 |

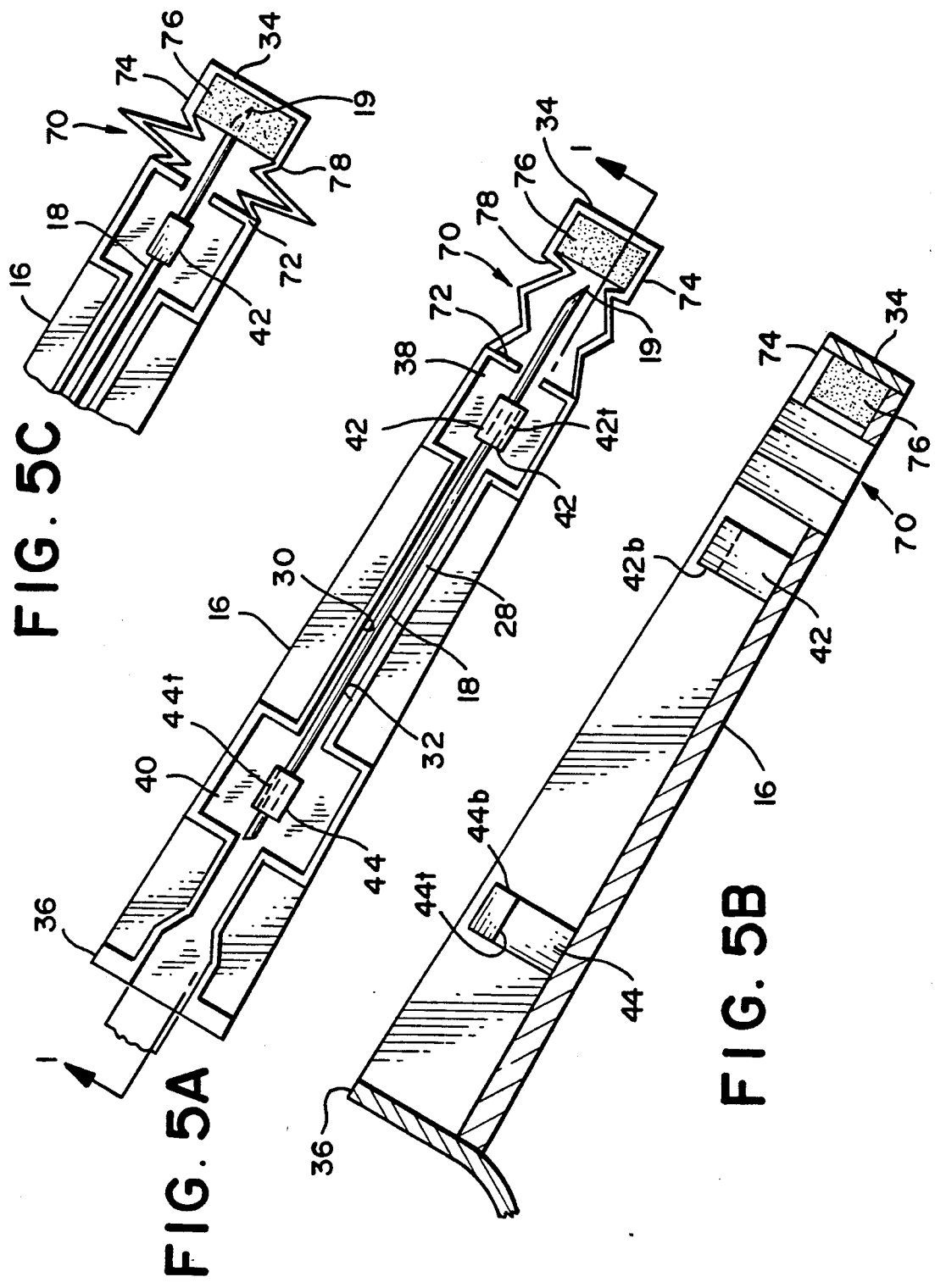

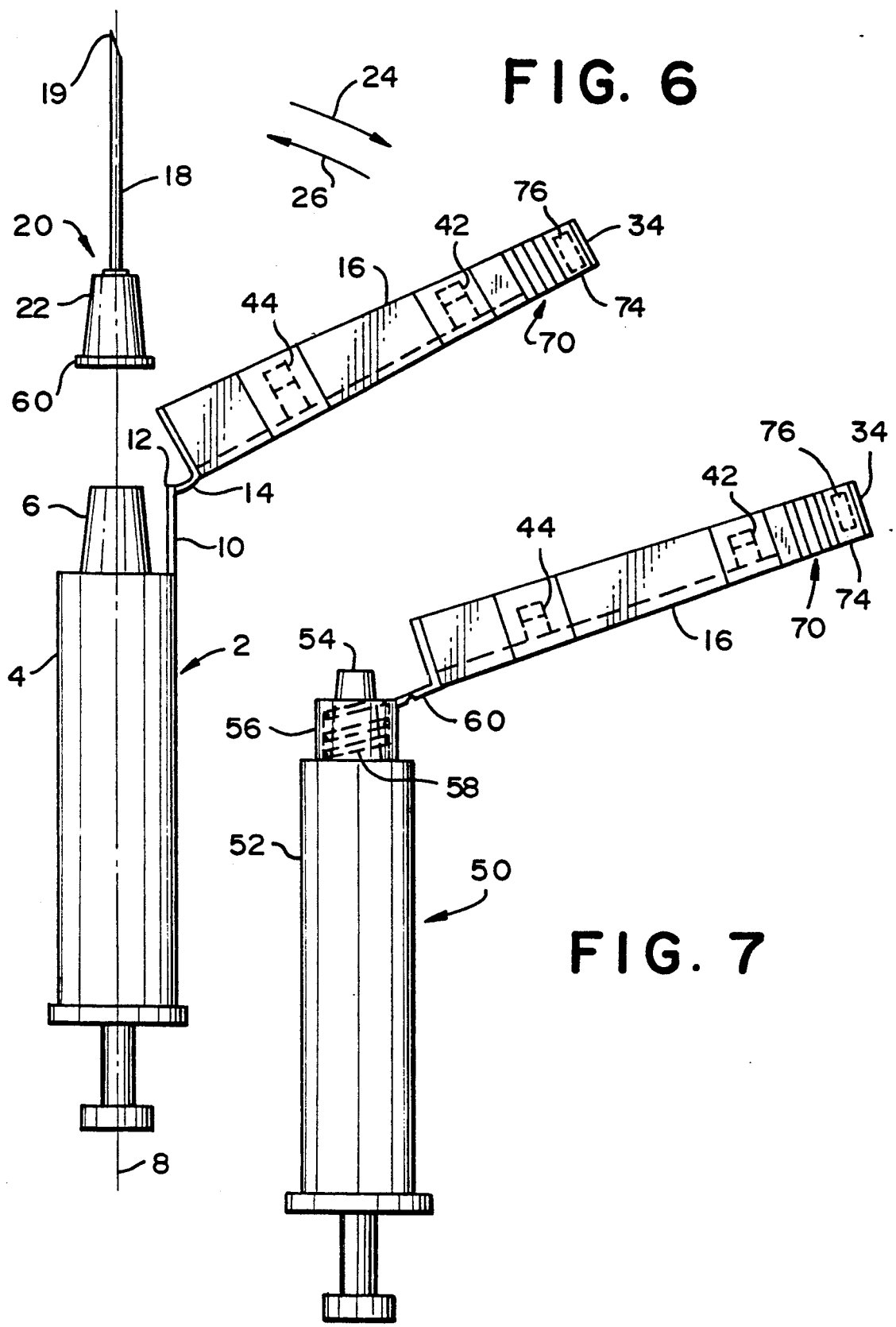

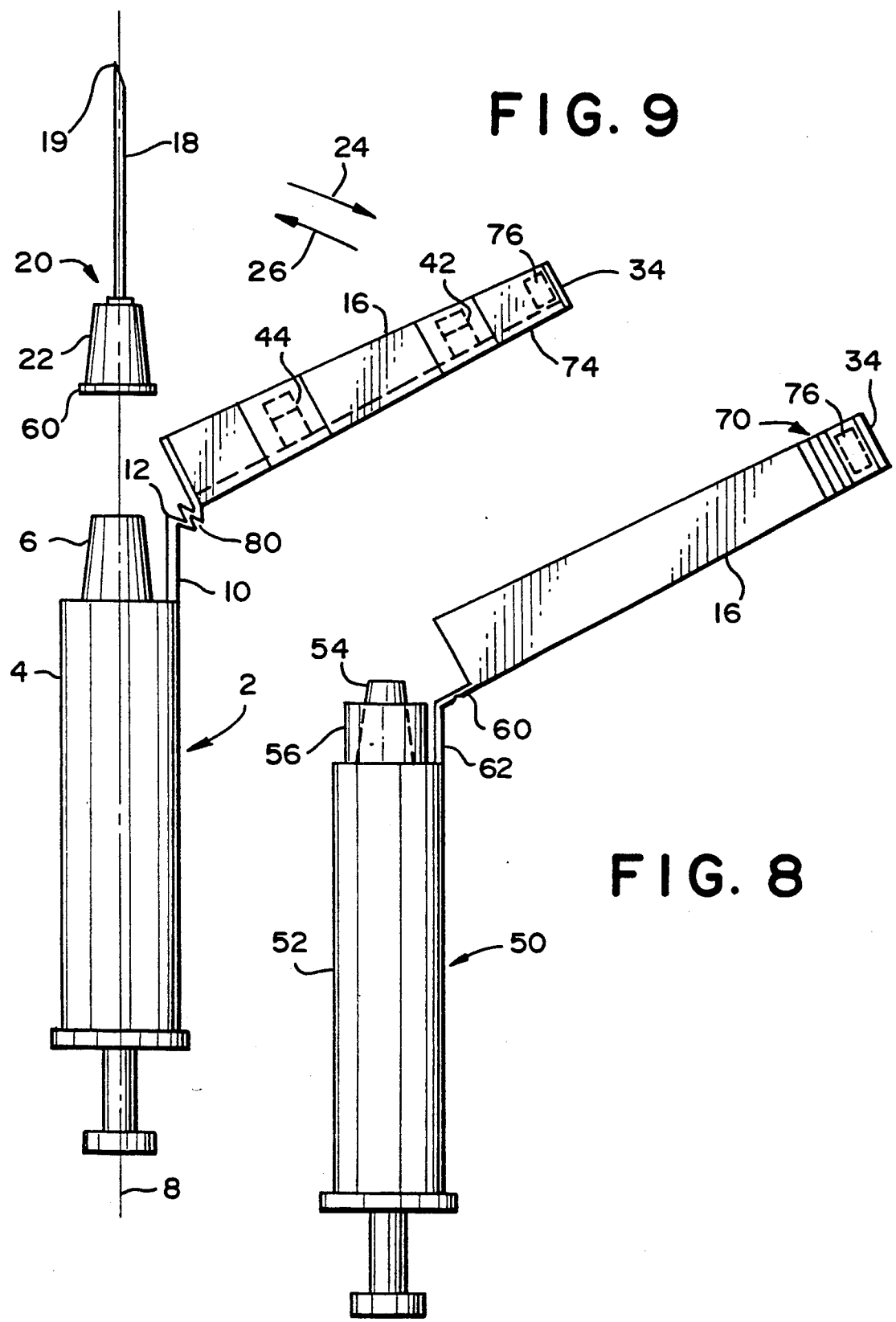

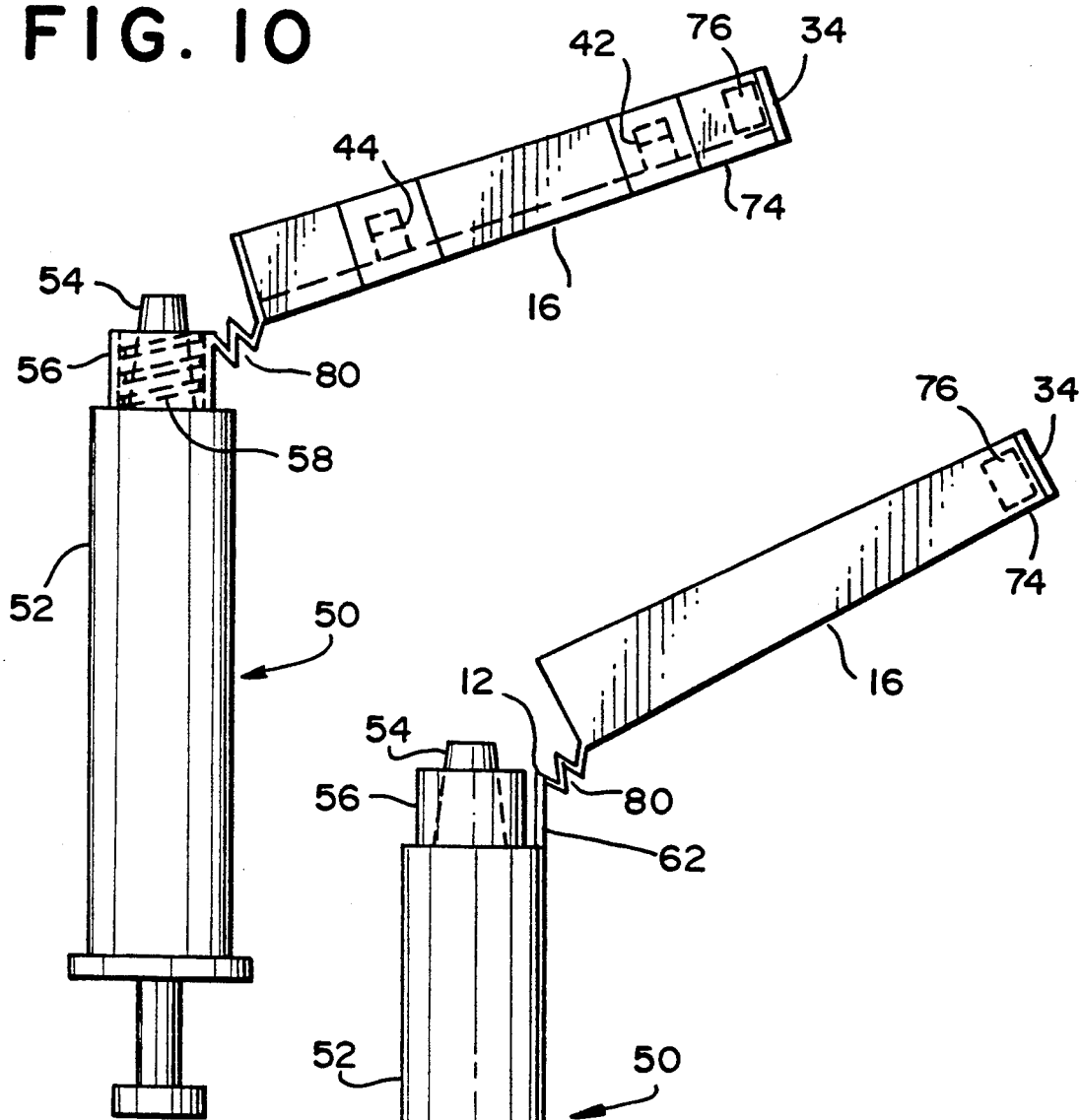

SYRINGE WITH PROTECTIVE HOUSING

FIELD OF THE INVENTION

This invention is related to co-pending U.S. patent application Ser. No. 532,558 entitled "Safety Needle Container" filed Jun. 4, 1990 now U.S. Pat. No. 4,982,842; co-pending U.S. patent application Ser. No. 561,459 entitled "Safety Needle Container" filed Aug. 1, 1990; and co-pending U.S. patent application Ser. No. 663,454 entitled "Needle Protection Device" filed Mar. 4, 1991 now U.S. Pat. No. 5,139,489. All of the cited co-pending applications have the same named inventor and are assigned to the same assignee as the instant invention.

Specifically, the present invention relates to a syringe that has connected thereto a protective housing to protect a user, or others, from being accidentally pricked by the sharp end of a needle mated to the syringe.

BACKGROUND OF THE INVENTION

Different devices for protecting a user, or others, from the sharp end of an exposed needle are disclosed in the aforenoted co-pending applications. Such protective devices safeguard the user, and bystanders, from being inadvertently punctured by contaminated needles and thereby risking contracting contagious diseases that may be carried by the contaminated needles.

To ensure a high degree of safety, it has been well recognized that no contact be made with a contaminated needle, after the same has been withdrawn from a patient Yet with conventional syringes, a contaminated needle has to be first recapped, and then removed from the syringe before it can be disposed of. During the process of recapping and removing the contaminated needle from the syringe, there is always the possibility that a user, or others, may be accidentally pricked by the contaminated needle.

SUMMARY OF THE PRESENT INVENTION

To eliminate as much as possible the possibility of accidental puncture by a contaminated needle, the present invention syringe comprises, in addition to the main body of the syringe, a protective housing connected thereto. Before use, the protective housing is pivoted away from the syringe so that a needle assembly may be mated to the syringe. After use, and specifically after the needle of the needle assembly has been withdrawn from the patient, the housing is pivoted (by possibly pushing the end portion of the housing against a stationary object) to a position in alignment with the needle so that the latter is enveloped by the former. At the same time, integral locking mechanisms within the housing would fixedly retain the needle within the housing. The syringe, with the contaminated needle securely retained within its integral housing, can then be safely disposed of.

To provide additional safety, a second feature of the present invention provides for the adaption of a sealing material at the distal (or end cap) portion of the housing which, when operated in conjunction with either a collapsible section integrally interposed between the main portion and the cap portion of the housing, or a collapsible living hinge connecting the housing to the syringe, would sealingly secure the tip of the contaminated needle. This enhanced safety feature further decreases the possibility of the user or bystanders from being exposed to the tip of a contaminated needle.

An objective of the present invention is, therefore, to provide a one piece disposable syringe that substantially reduces the potential risk of a user, or others, from inadvertently being pricked by a contaminated needle.

Another objective of the present invention is to provide a one piece disposable syringe that has redundant safety features built in to thereby doubly ensure that the tip of a contaminated needle does not pose a risk to a user, or others.

BRIEF DESCRIPTION OF THE DRAWINGS

The above-mentioned objectives and advantages of the present invention will become more apparent and the invention will best be understood by reference to the following description of embodiments of the present invention taken in conjunction with the accompanying drawings, wherein:

FIG. 5A is a plan view of a variant of the FIG. 2A protective housing;

FIG. 5B is a cross-sectional view of the FIG. 5A protective housing;

FIG. 5C is a partial view of the FIG. 5A variant housing whose collapsible section has been compressed;

FIG. 6 is a side view of a variant of the FIG. 1 embodiment whose protective housing has been replaced by the FIG. 5A protective housing;

FIG. 7 is a side view of a variant of the FIG. 3 embodiment whose housing has been replaced by the FIG. 5A protective housing;

FIG. 8 is a variation of the FIG. 4 embodiment whose housing has been replaced by the FIG. 5A protective housing;

FIG. 9 is another variation of the FIG. 1 embodiment whose housing has adapted at its distal end section a sealing member and whose housing is connected to the syringe by a collapsible hinge;

FIG. 10 is another variation of the FIG. 3 embodiment whose housing has adapted at its distal end a sealing material and whose housing is connected to the syringe via a collapsible hinge; and FIG. 11 is another variation of the FIG. 4 embodiment whose housing has adapted at its distal end a sealing material and whose housing is connected to the syringe by a collapsible living hinge.

DETAILED DESCRIPTION OF THE INVENTION

Figure 1:
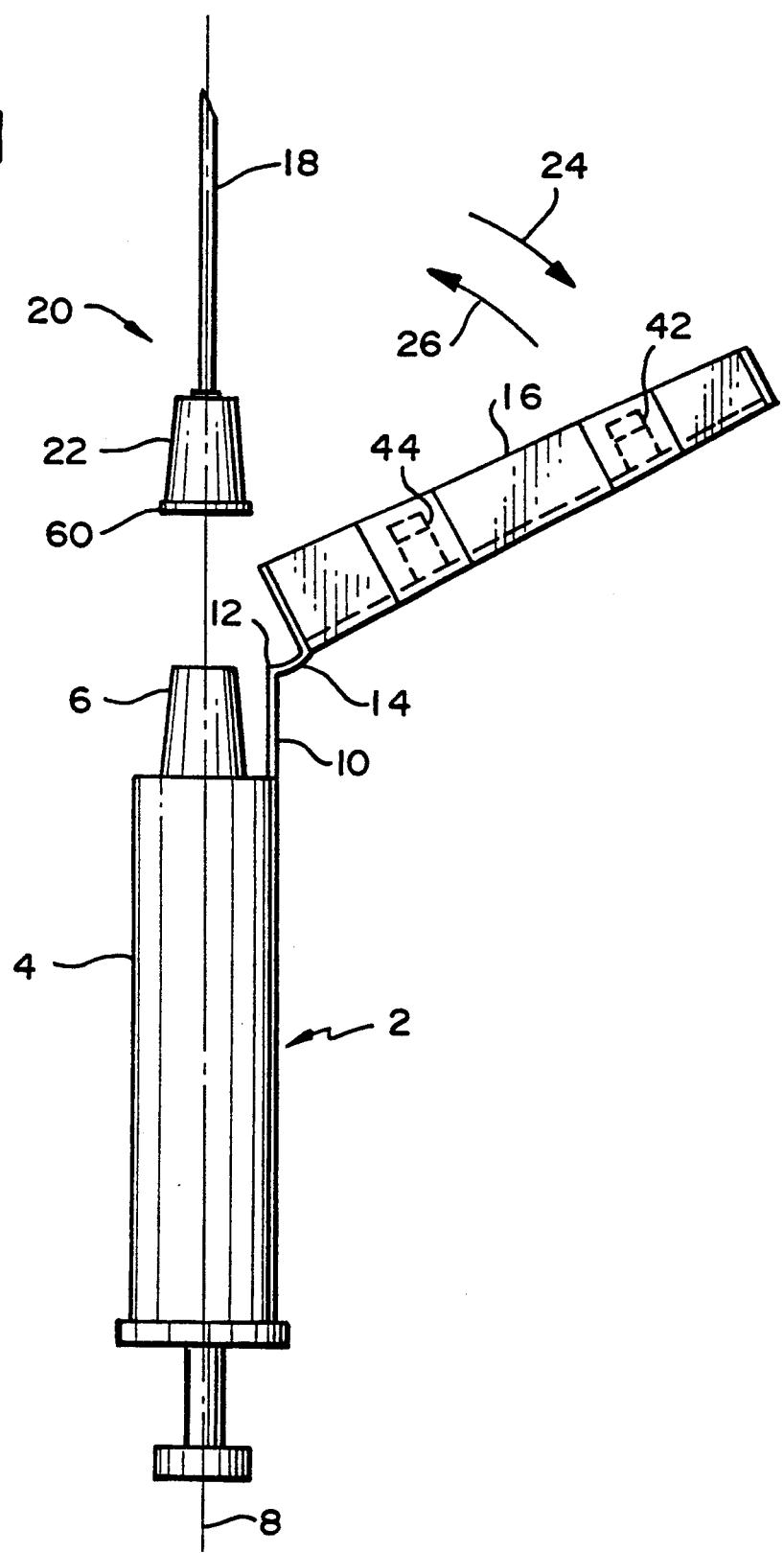
FIG. 1 is a side view of a first embodiment of the syringe of the present invention drawn in alignment with a needle assembly that is to be mated to the syringe.

A first embodiment of the present invention comprising a luer slip type syringe 2 is shown in FIG. 1. As illustrated, syringe 2 has a main body portion 4 and a protrusion, or a male luer ejection end, 6 integrally extending from main body portion 4. Extending from main body portion 4 longitudinally along axis 8 is a shoulder member 10. At distal end 12 of shoulder member 10 there is connected, via a hinge means such as living hinge 14, a housing or sheath 16. It should be appreciated that the length of shoulder member 10 may vary, depending on the type and length of needle being used with the syringe, or the length and size of ejection end 6. In fact, shoulder member 10 does not necessarily have to be there, inasmuch as hinge 14 may be directly integrated to main body portion 4. Similarly, the length of housing 16 may vary, dependent on the length of cannula 18 of needle assembly 20, so as to be adaptable to any needle length To mate needle assembly 20 to syringe 2, needle hub 22 of needle assembly 20 is slip fitted over ejection end 6. As should be apparent, housing 16 had already been pivoted out of the way of cannula 18 along the direction indicated by arrow 24. After use (i.e., after cannula 18 has been withdrawn from the patient), housing 16 is pivoted along the direction indicated by arrow 26 to envelop cannula 18.

To substantially fixedly retain cannula 18 within housing 16 to thereby prevent relative movement between cannula 18 and housing 16, the locking mechanisms disclosed in aforenoted co-pending U.S. patent application Ser. No. 532,558, the disclosure of which is incorporated herein by reference, is used.

Briefly, with reference to FIGS. 2A-2C, it can be seen that longitudinal housing 16 has an elongated slot 28 bounded by sides 30 and 32, running substantially in parallel along the length of housing 16, which has a tip 34 and a base 36. (For one-handed operation, a user would push the portion of housing 16 near tip 34 against a stationary object to pivot housing 16 into alignment with cannula 18.) Further shown on housing 16 are openings 38 and 40, at whose respective centers are integrally formed locking mechanisms 42 and 44. Locking mechanisms 42 and 44 each have a substantially rigid finger, respectively 42a and 44a.

Refer now to FIG. 2C and representative locking mechanism 42. As housing 16 is pivoted into alignment with cannula 18, cannula 18 is first biased against finger 42a. But as cannula 18 relatively moves past tip 42t of finger 42a, the previously biased finger 42a would spring back to its natural position to thereby retain cannula 18 within the space between finger 42a and extension 42b, and substantially prevent relative movement between cannula 18 and housing 16.

FIG. 2B is a cross-sectional view, along cut A—A of FIG. 2A, of housing 16 which shows that fingers 42a and 44a extend in opposite downwardly sloping directions. Such a construction makes it more difficult for a retained cannula from being forcibly removed from the housing.

Figures 3, 4:
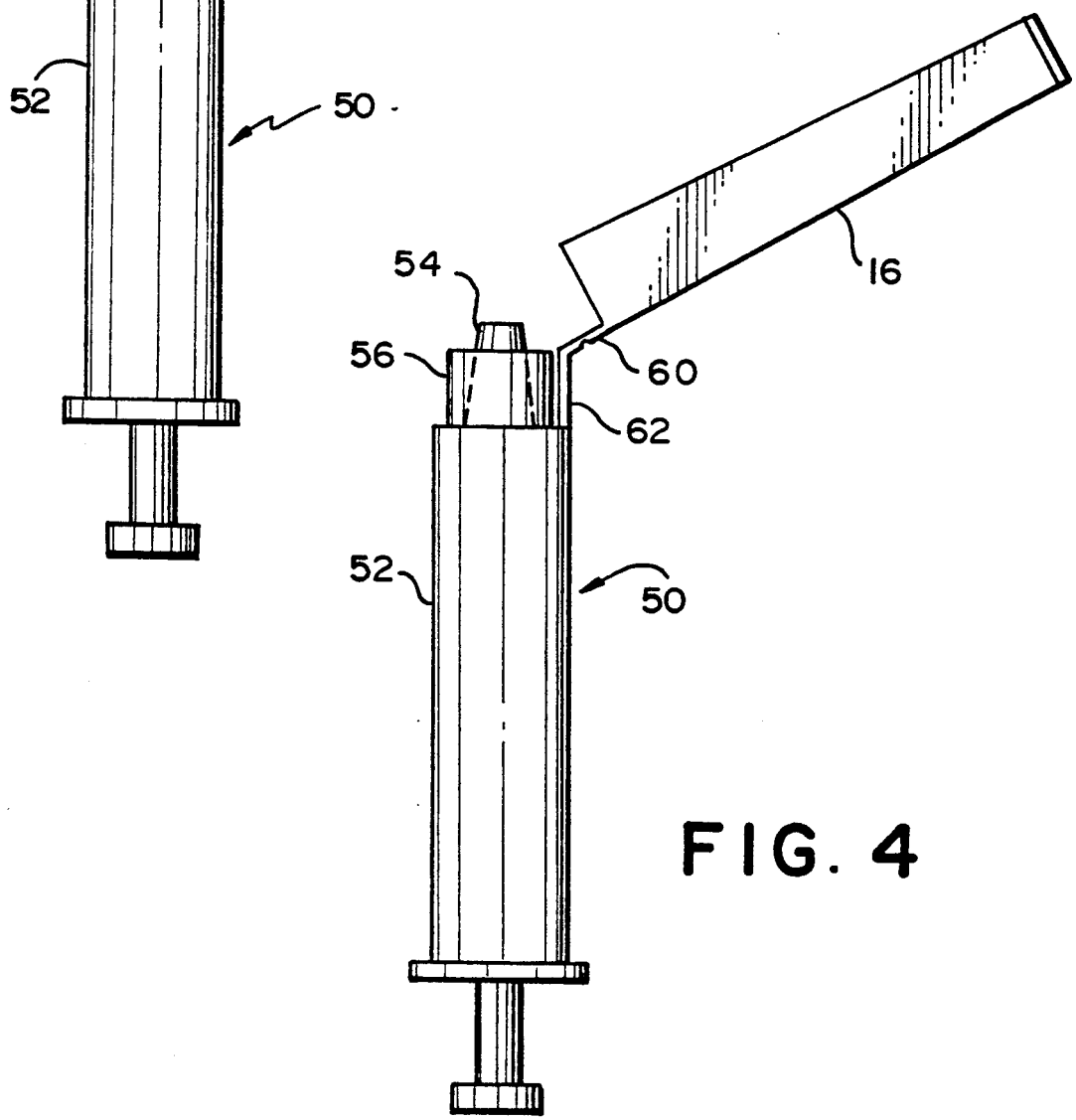
FIG. 3 is a second embodiment of the syringe of the present invention.
FIG. 4 is yet another embodiment of the syringe of the present invention.

A second embodiment of the present invention is illustrated in FIG. 3 where protective housing 16 is shown to be connected to a luer lock type syringe 50. Like the luer slip type syringe, luer lock type syringe 50 has a main body portion 52 and an ejection end 54. Furthermore, a collar 56 having internal threads 58 integrally extends from main body portion 52 to surround the lower portion of ejection end 54. For the FIG. 3 embodiment, needle assembly 20 (see FIG. 1) is mated to syringe 50 by threadedly mating extension 60 at the end of hub 22 with threads 58 of collar 56. Hub 22 naturally becomes mated with ejection end 54. Protective housing 16 is shown to be connected to collar 56 by a living hinge 60, whose length, as should be appreciated, can be varied depending on the length of the cannula of the needle assembly mated to syringe 50.

Another embodiment of the present invention is shown in FIG. 4. The only difference between the FIG. 3 and FIG. 4 embodiments is the interposing of a shoulder member 62, which extends integrally from main body portion 52 of syringe 50, between housing 16 and main body portion 52. As should be appreciated, the length of shoulder member 62 may be varied in accordance with need. Further, it should be appreciated that shoulder member 62 may actually be jointedly connected to an outer circumferential portion of collar 56.

In operation, each of the embodiments of the present invention is to be mated with a needle assembly, such as 20 shown in FIG. 1. In the case of the FIG. 1 embodiment, needle hub 22 is slip fittedly mated with ejection end 6 of syringe 2. For the case of syringe 50 shown in FIGS. 3 and 4, extension 60 of needle hub 22 threadedly mates with the internal threads of collar 56 to join the needle assembly to the syringe. In any one of the embodiments, before use, housing 16 is pivoted in a direction as shown by arrow 24 (FIG. 1) away from cannula 18. After cannula 18 has been removed from a patient, housing 16 is pivoted along the direction indicated by arrow 26, via hinge 14 (or 60 for the FIGS. 3 and 4 embodiments) into alignment with cannula 18. At which time at least one of locking mechanisms 42 and 44 would fixedly retain cannula 18 within housing 16 to prevent relative movement between cannula 18 and housing 16. Having thus enveloped and substantially fixedly retained cannula 18, the syringe may be disposed of.

Figure 2:
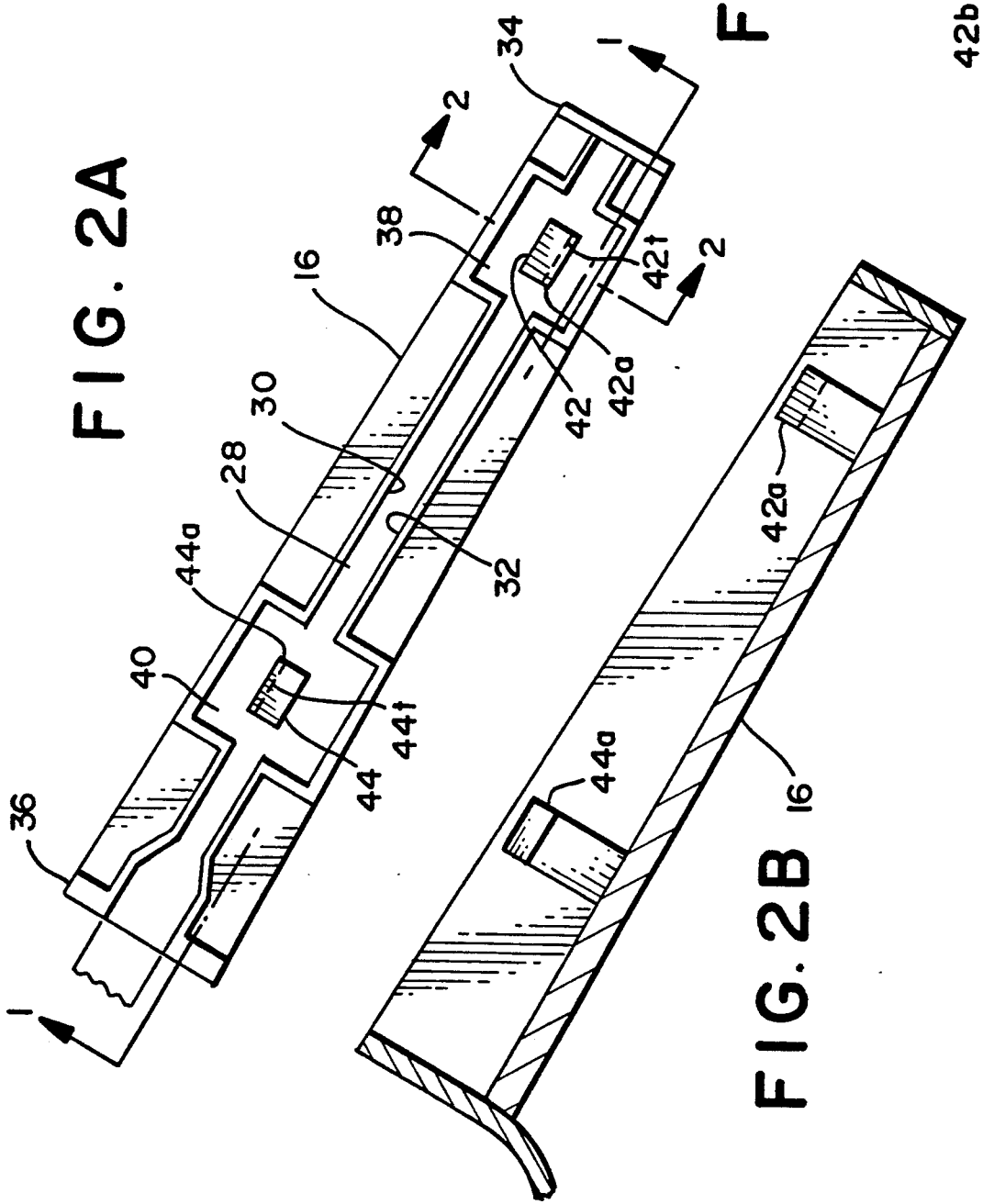
FIG. 2A is a plan view of the protective housing shown in the FIG. 1 embodiment.
FIG. 2B is a cross-sectional cut-away view, along line A—A, of the FIG. 2A protective housing.
FIG. 2C is a cross-sectional cut-away view, along line B—B, of the FIG. 2A protective housing.

With reference to FIGS. 5A-5C, a variant of the FIG. 2A housing may also be used with the instant invention to further enhance the safety integrity of the present invention by ensuring that the tip of a contaminated needle (or cannula) is sealingly secured, and therefore not be exposed, even in highly unlikely circumstances where the protective housing may not properly retain the contaminated needle—as for example when the housing is cracked or the locking mechanisms malfunctioned. For the FIG. 5A variant, elements which are similar, or perform similar functions, as those of the embodiments shown in FIGS. 1-4 are labelled the same.

As illustrated in FIG. 5A, variant housing 16 has a substantially longitudinal collapsible (compressible or crushable) accordion-shaped section 70 interposed between and integrally connecting the main portion and a cap portion 74 of housing 16. For purposes of explanation, the main portion of housing 16 extends from base 36 to a partition 72 at the end of opening 38 If the housing is to be a one-piece molded sheath, manufactured for example from plastic, collapsible section 70 becomes an integral part of housing 16 by integrally extending from partition 72 to edge 78 of cap portion 74. Alternatively, collapsible section 70 may be made of materials different from that of housing 16, as for example foldable cardboard or fibered paper, as long as the main portion of housing 16 may be jointed to cap portion 74 by the collapsible section.

Although collapsible section 70 is shown to be accordion-shaped, it should be appreciated that differently shaped collapsible sections may also be used, so long as such sections are collapsible (compressible or crushable) to thereby enable the distance separating the main portion and cap portion 74 of housing 16 (or more accurately, the distance between partition 72 and edge 78) to be reduced as relative movement urging the main portion and cap portion 74 of housing 16 toward each other is effected.

As shown, adapted to and fitted within cap portion 74 is a sealing material 76 which may be, for example, a malleable elastomer, rubber or some other suitable material that can sealingly secure and firmly grip a sharp object, as for example tip 19 of needle 18, penetrating therein. Materials such as cork or wax may also be used. It should further be appreciated that tip 34 of cap portion 74 is made of a material such as hard plastic that is substantially impervious to penetration by sharp objects such as, for example, tip 19 of needle 18. As has been pointed out previously, the length of housing 16, which extends from base 36 to tip 34, may vary to accommodate various lengths of needle 18, and is such that a clearance is provided in the space within collapsible portion 70 to allow a needle of any given length to pass unobstructed through opening 28, when housing 16 is pivoted to substantially align and envelop needle 18.

Assume that housing 16 has been pivoted into alignment with the longitudinal axis of needle 18 and that needle 18 has in turn been retained by at least one of locking mechanisms 44 and 42. As best shown in FIG. 5C, when relative movement for urging cap portion 74 toward the main portion of housing 16 is effected, collapsible section 70 would collapse (or be compressed) to reduce the distance separating partition 72 and edge 78, and thereby effectively cause sealing material 76 to move toward tip 19 of needle 18 and be penetrated thereby Once having been penetrated, sealing material 76 substantially and sealingly secures tip 19 of needle 18. The relative movement between the main portion of housing 16 and cap portion 74 may be effected by a single-handed operation of pushing tip 34 of housing 16 against some immobile object FIG. 5B provides for a side view of the FIG. 5A variant protective housing.

FIGS. 6, 7 and 8 respectively show the corresponding housings of the embodiments of FIGS. 1, 3 and 4 to have been substituted for by the FIG. 5A variant protective housing. Thus, each of the alternative embodiments of FIGS. 6, 7 and 8 provides the additional safety feature of sealingly securing the tip of a contaminated needle. This is achieved, of course, by cap portion 74 being urged against tip 19 of needle 18, after variant housing 16 has been pivoted into alignment position with the contaminated needle, such that the tip of the needle pierces and penetrates into sealing material 76, which is adapted within cap portion 74, and be sealingly secured thereby.

Instead of a housing having a main portion jointed to cap portion 74 by a collapsible section, an alternative embodiment for securely retaining the tip of a contaminated needle may be had with reference to FIGS. 9, 10 and 11. Again, components in FIGS. 9, 10 and 11 which are similar to, or perform similar functions as, those discussed earlier are labeled the same.

With particular reference to FIG. 9, which is a variant of the FIG. 1 embodiment, it can be seen that housing 16, which is a unitary piece, is flexibly connected to distal end 12 of shoulder member 10 by a collapsible hinge means such as living hinge 80. Housing 18 has a cap portion 74 within which a sealing material 76 is adaptedly fitted.

As should be readily appreciated, after housing 16 has been pivoted into alignment position along the longitudinal axis of needle 18, a relative movement may be effected to urge housing 16 and syringe 2 toward each other so that collapsible hinge 80 would collapse (or be compressed), to thereby cause tip 19 of needle 18 to pierce and penetrate into sealing material 76 and be sealingly gripped thereby. As should further be appreciated, it is not necessary that shoulder member 10 be present for the FIG. 9 embodiment, as collapsible hinge 80 may be directly connected to syringe 2.

In FIG. 10, housing 16 is shown to be directly connected to collar 56 of luer lock type syringe 50. Do note, however, that the length of collapsible living hinge 80 may vary, and that housing 16 may be connected, via collapsible hinge 80, directly to main body portion 52 of syringe 50.

The variant embodiment of the present invention syringe illustrated in FIG. 11 shows that housing 16 is connected to syringe 50 at distal end 12 of extending shoulder member 62. Of course, the length of shoulder member 62 may be varied in accordance with need. Or, for that matter, collapsible hinge 80 can directly connect housing 16 to syringe 50, thereby bypassing shoulder member 62 altogether. Further, the operation of the variant embodiments shown in FIGS. 9, 10 and 11 is the same in that each requires that housing 16 be pivoted into alignment position with needle 18, which is then substantially retained by at least one of locking mechanisms 42 and 44. And by relatively moving housing 16 and main body portion 52 of syringe 50 toward each other (as for example by urging tip 34 of housing 16 against some immobile object), collapsible hinge 80 would collapse (be compressed or crushed) so that tip 19 of needle 18 is caused to pierce and penetrate into sealing material 76 and be sealingly retained thereby.

With the embodiments illustrated in FIGS. 6–11, the safety integrity of the syringe of the instant invention is further enhanced in that, in addition to having the contaminated needle substantially permanently retained within a protective housing, the tip of the contaminated needle is also substantially sealingly secured within a sealing material.

Inasmuch as the present invention is subject to many variations, modifications and changes in detail, it is intended that all matter described throughout this specification and shown in the accompanying drawings be interpreted as illustrative only and not in a limiting sense. Accordingly, it is intended that the invention be limited only by the spirit and scope of the hereto appended claims.

I claim:

1. A syringe having a main body portion and a protrusion extending therefrom to slip-fittedly mate with the hub of a needle, comprising housing means flexibly connected to said main body portion, and pivotable toward a position in substantial alignment along the longitudinal axis of said needle for enveloping said needle, said housing means including locking means for substantially fixedly retaining said needle within said housing means once said housing means has been pivoted to said position.

2. Syringe of claim 1, further comprising:

a shoulder member extending longitudinally from said main body portion to connect said housing means.

3. Syringe of claim 1, wherein said housing means is integrally and flexibly connected to said main body portion via a hinge means.

4. Syringe of claim 1, wherein said housing means comprises a longitudinal sheath having an elongated slot through which said needle passe when said sheath is pivoted to said position.

5. Syringe of claim 1, wherein said locking means housing means for substantially preventing relative movement between said needle and said housing means.

6. Syringe of claim 1, wherein said housing means comprises:
   a main section;
   a cap section;
   a collapsible section interposed between and connecting said main and cap sections; and
   means adapted within said cap section for sealingly securing the tip of said needle after said housing means has been pivoted to said position and said main and cap sections have been effectively urged toward each other to collapse said collapsible section to thereby cause the tip of said needle to penetrate into said sealing means.

7. Syringe of claim 1, wherein said housing means is flexibly connected to said main body portion via a collapsible hinge means; and
   wherein said housing means includes a cap section to which a sealing means is adapted, said sealing means sealingly securing the tip of said needle after said housing means has been pivoted to said position and effectively urged toward said syringe along the longitudinal axis of said needle to thereby collapse said collapsible hinge means and cause the tip of said needle to penetrate into said sealing means.

8. A safety device for preventing accidental pricking by a needle, comprising:
   a syringe having a main body portion and an ejection end extending therefrom for mating with said needle;
   housing means flexibly connected to said syringe, said housing means pivotable to a position in substantial alignment along the longitudinal axis of said needle for enveloping said needle;
   locking means integral of said housing means for substantially fixedly retaining said needle to prevent relative movement between said needle and said housing means once said housing means has been pivoted to said position.

9. Safety device of claim 8, further comprising:
   a shoulder member extending longitudinally from said main body portion to connect said housing means.

10. Safety device of claim 8, wherein said housing means is integrally and flexibly connected to said syringe via a hinge means.

11. Safety device of claim 8, wherein said housing means comprises a longitudinal sheath having an elongated slot through which said needle passes when said sheath is pivoted to said position.

12. Safety device of claim 8, wherein said locking means comprises at least one hooking means integral of said housing means.

13. Safety device of claim 8, wherein said housing means comprises:
   a main section;
   a cap section;
   a collapsible section interposed between and connecting said main and cap sections; and
   means adapted within said cap section for sealingly securing the tip of said needle after said housing means has been pivoted to said position and said main and cap sections have been effectively urged toward each other to collapse said collapsible section to thereby cause the tip of said needle to penetrate into said sealing means.

14. Safety device of claim 8, wherein said housing means is flexibly connected to said syringe via a collapsible hinge means; and
   wherein said housing means includes a cap section to which a sealing means is adapted, said sealing means sealingly securing the tip of said needle after said housing means has been pivoted to said position and effectively urged toward said syringe along the longitudinal axis of said needle to thereby collapse said collapsible hinge means and cause the tip of said needle to penetrate into said sealing means.

15. A safety device for preventing accidental pricking by a needle, comprising:
   a syringe having a main body portion, an ejection end extending therefrom and an internally threaded collar extending from said main body portion to surround at least a portion of said ejection end for mating with said needle;
   housing means flexibly connected to said syringe, said housing means pivotable to a position in substantial alignment along the longitudinal axis of said needle for enveloping said needle;
   locking means formed within said housing means for substantially fixedly retaining said needle to prevent relative movement between said needle and said housing means once said housing means has been pivoted to said position.

16. Safety device of claim 15, wherein said housing means is hingedly connected to said collar of said syringe.

17. Safety device of claim 15, wherein said housing means is integrally connected to said syringe via a hinge means 18. Safety device of claim 15, further comprising:
   a shoulder member extending longitudinally from said main body portion of said syringe to connect said housing means.

19. Safety device of claim 15, wherein said housing means comprises a longitudinal sheath having an elongated slot through which said needle passes when said sheath is pivoted to said position.

20. Safety device of claim 15, wherein said locking means comprises at least one hooking means integral of said housing means.

21. Safety device of claim 15, wherein said housing means comprises:
   a main section;
   a cap section;
   a collapsible section interposed between and connecting said main and cap sections; and
   means adapted within said cap section for sealingly securing the tip of said needle after said housing means has been pivoted to said position and said main and cap sections have been effectively urged toward each other to collapse said collapsible section to thereby cause the tip of said needle to penetrate into said sealing means.

22. Safety device of claim 15, wherein said housing means is flexibly connected to said syringe via a collapsible hinge means; and
   wherein said housing means includes a cap section to which a sealing means is adapted, said sealing means sealingly securing the tip of said needle after said housing means has been pivoted to said position and effectively urged toward said syringe along the longitudinal axis of said needle to thereby collapse said collapsible hinge means and cause the tip of said needle to penetrate into said sealing means.

* * * * *